United States Patent [19]

Johnson et al.

[11] Patent Number: 5,343,156

[45] Date of Patent: Aug. 30, 1994

[54] IC FOR PRODUCING AN OUTPUT VOLTAGE RELATED TO FUEL COMPOSITION IN A CAPACITIVE FUEL SENSOR

[76] Inventors: Nick M. Johnson, 11663 Par Ave., Los Altos, Calif. 94024; Chun-Foong Cheah, 1420 Turk St., #905, San Francisco, Calif. 94115

[21] Appl. No.: 868,604

[22] Filed: Apr. 15, 1992

[51] Int. Cl.$^5$ ............................................. G01R 27/26
[52] U.S. Cl. ................................... 324/672; 324/676; 324/679; 73/61.43; 73/118.1
[58] Field of Search ............... 324/663, 676, 677, 678, 324/679, 672; 73/61.43, 118.1

[56] References Cited

U.S. PATENT DOCUMENTS

| | | | |
|---|---|---|---|
| 3,818,877 | 6/1974 | Barrera et al. | 73/861.23 |
| 4,418,569 | 12/1983 | Kuhnel | 324/678 X |
| 4,470,300 | 9/1984 | Kobayashi | 324/677 X |
| 4,806,847 | 2/1989 | Atherton et al. | 324/678 X |
| 5,033,293 | 7/1991 | Honma et al. | 73/118.1 |

Primary Examiner—Kenneth A. Wieder
Assistant Examiner—Glenn W. Brown

[57] ABSTRACT

A circuit for responding to the output of a capacitive fuel sensor that can distinguish gasoline from methanol and produces an output that is related to the methanol proportion. The response is independent of the conductivity in the sensor resulting from fuel contamination. A square wave is employed to excite the sensor and the circuit provides for stabilizing the square wave amplitude. The circuit includes an amplitude modulation detector that converts the square wave transients into a fuel composition related voltage output that can be applied to an engine control mechanism that will adjust the automotive engine to operate efficiently with the fuel being supplied. Circuits are shown for linearizing the fuel composition to voltage response and a charge dispenser amplitude modulation detector is described wherein the detection occurs only during the square wave transient interval.

8 Claims, 5 Drawing Sheets

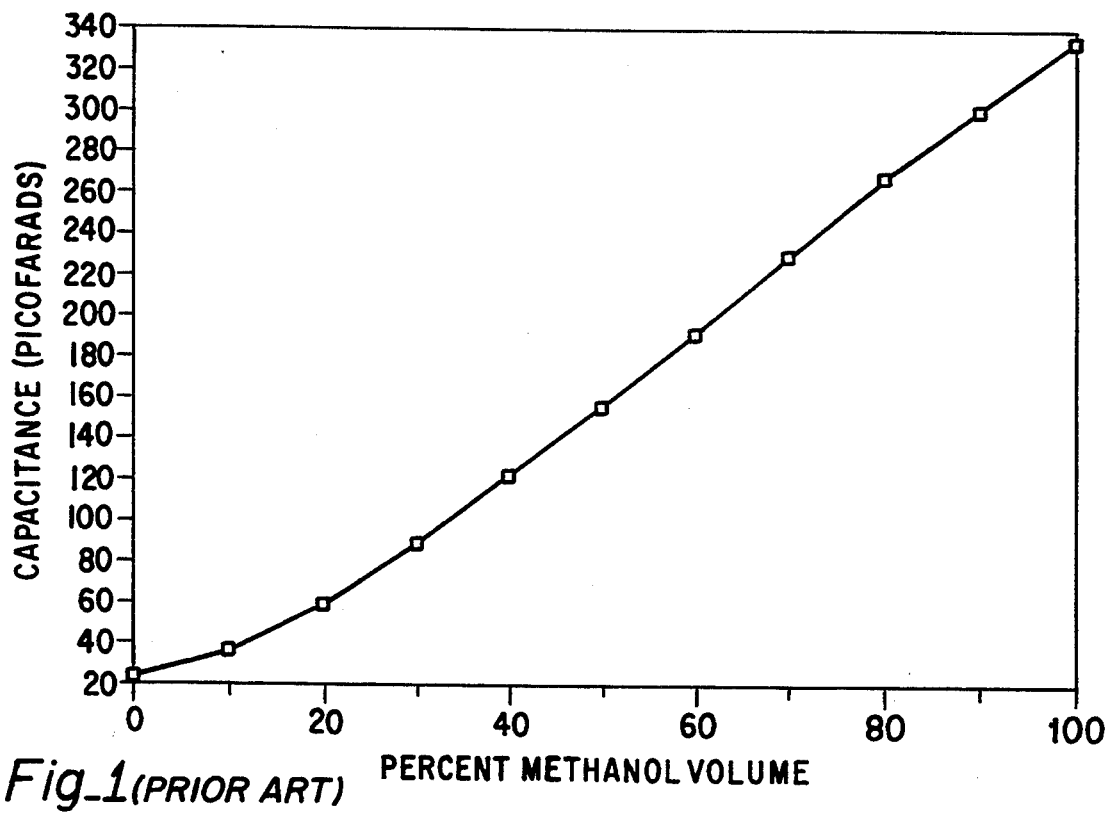
Fig_1 (PRIOR ART)
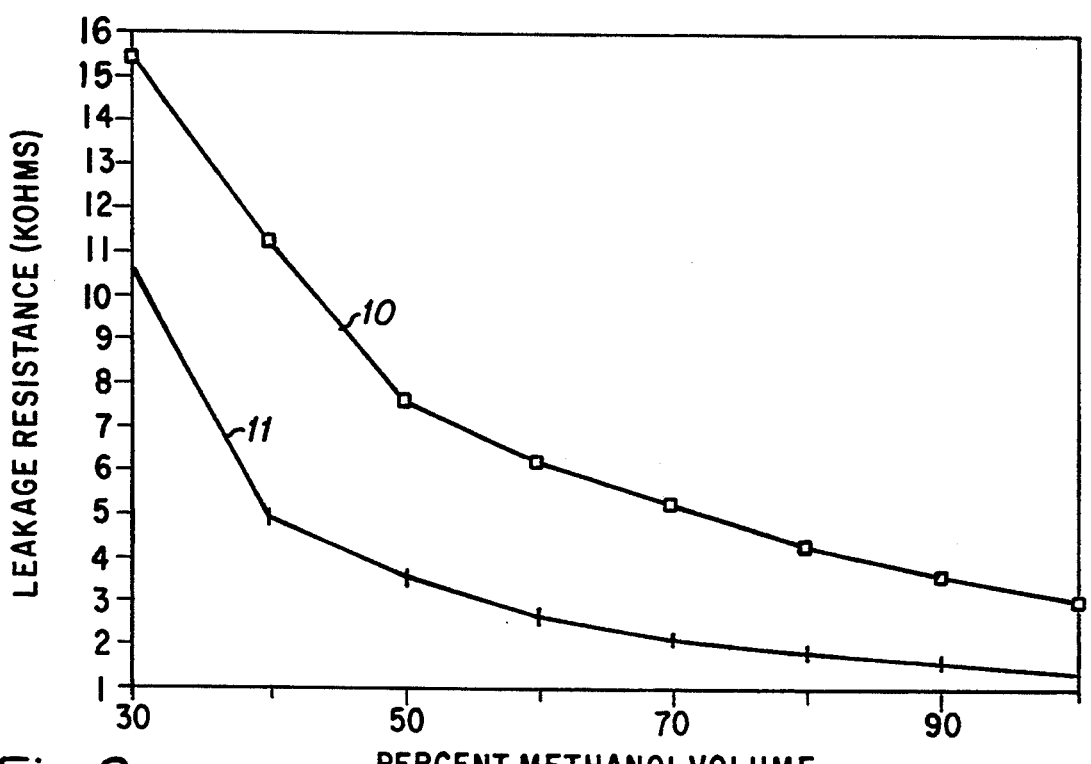
Fig_2 (PRIOR ART)

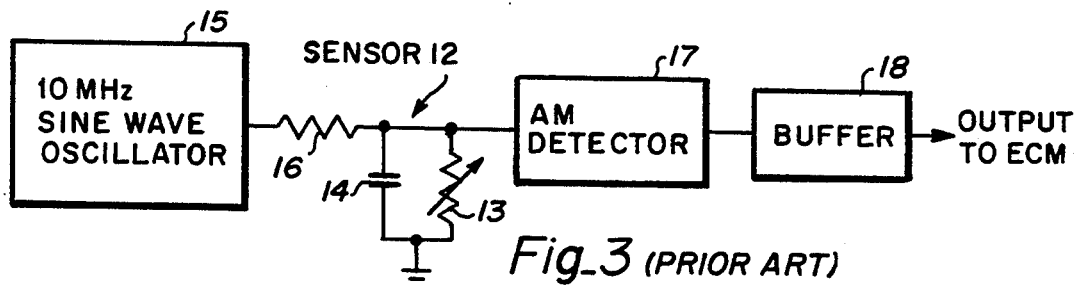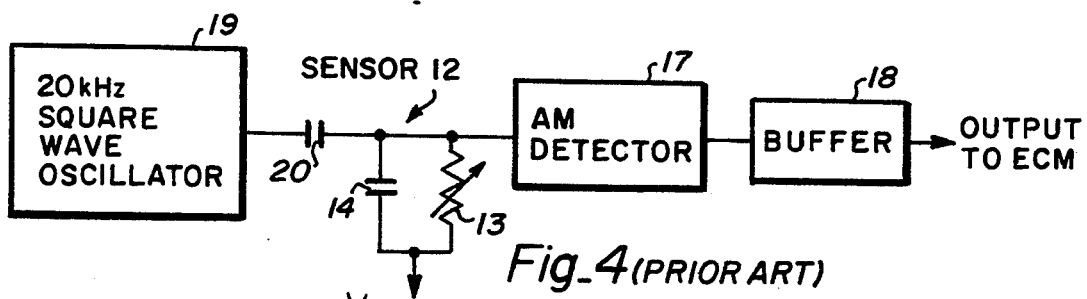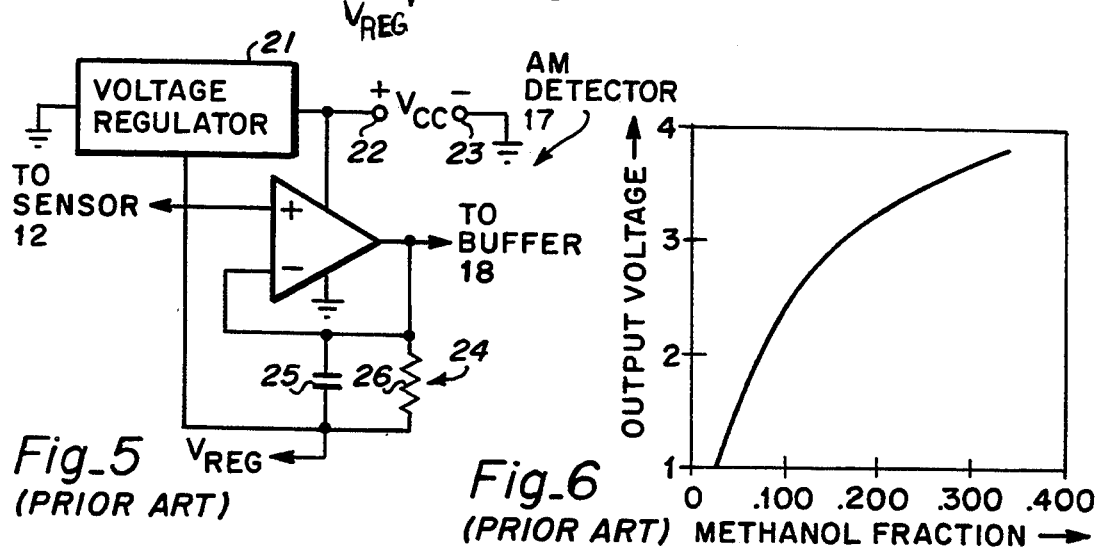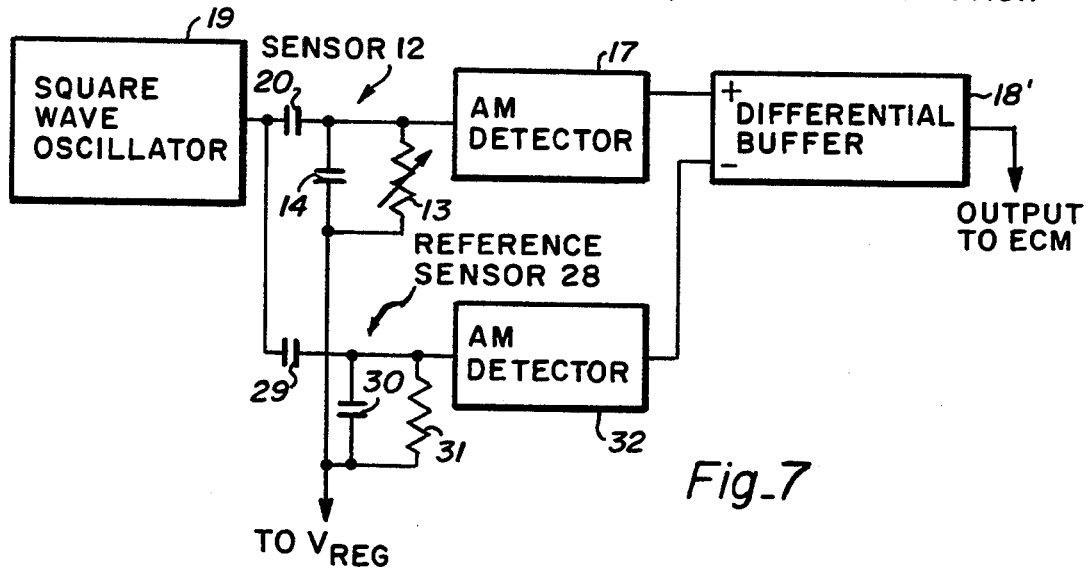

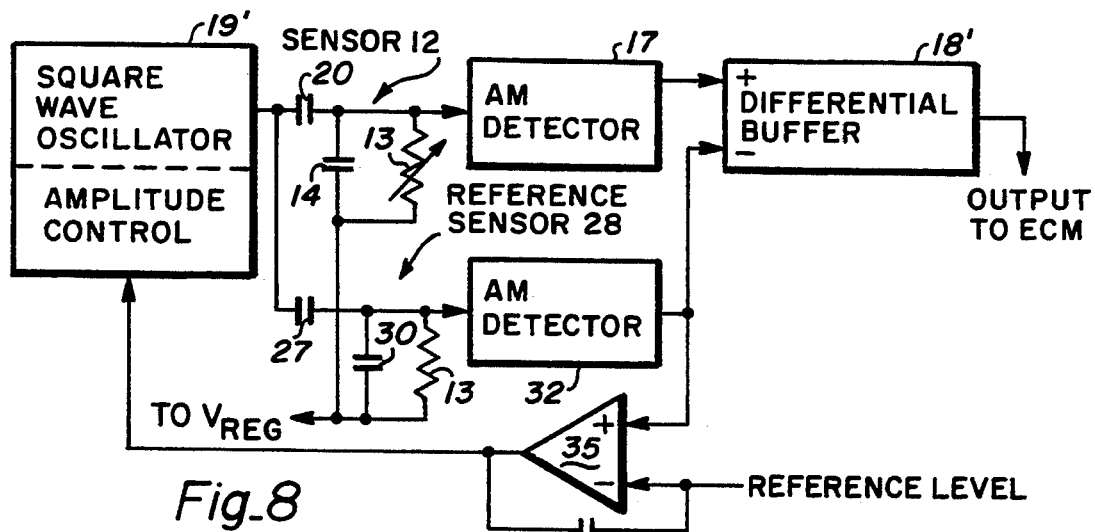
Fig_8
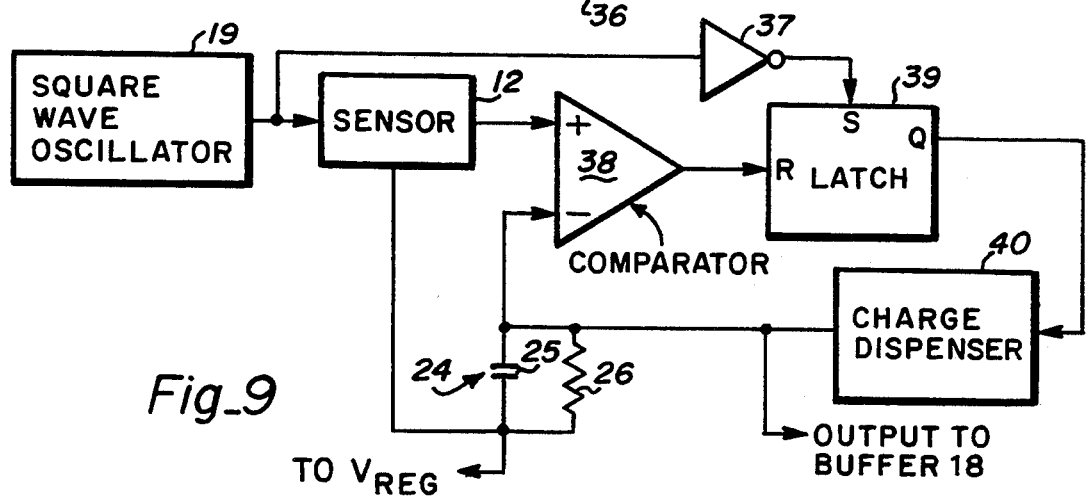
Fig_9
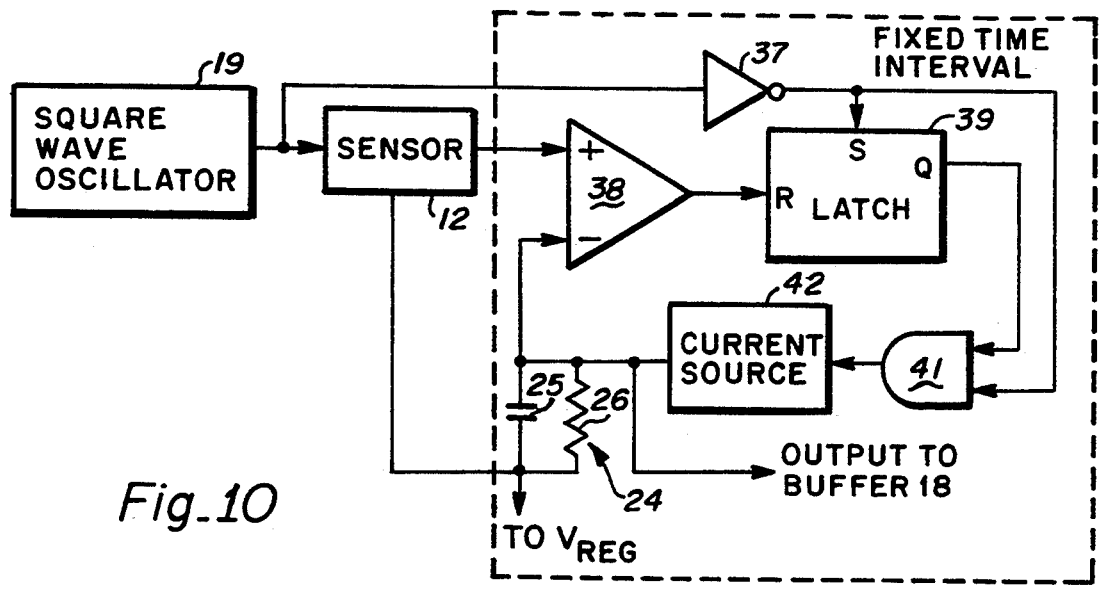
Fig_10

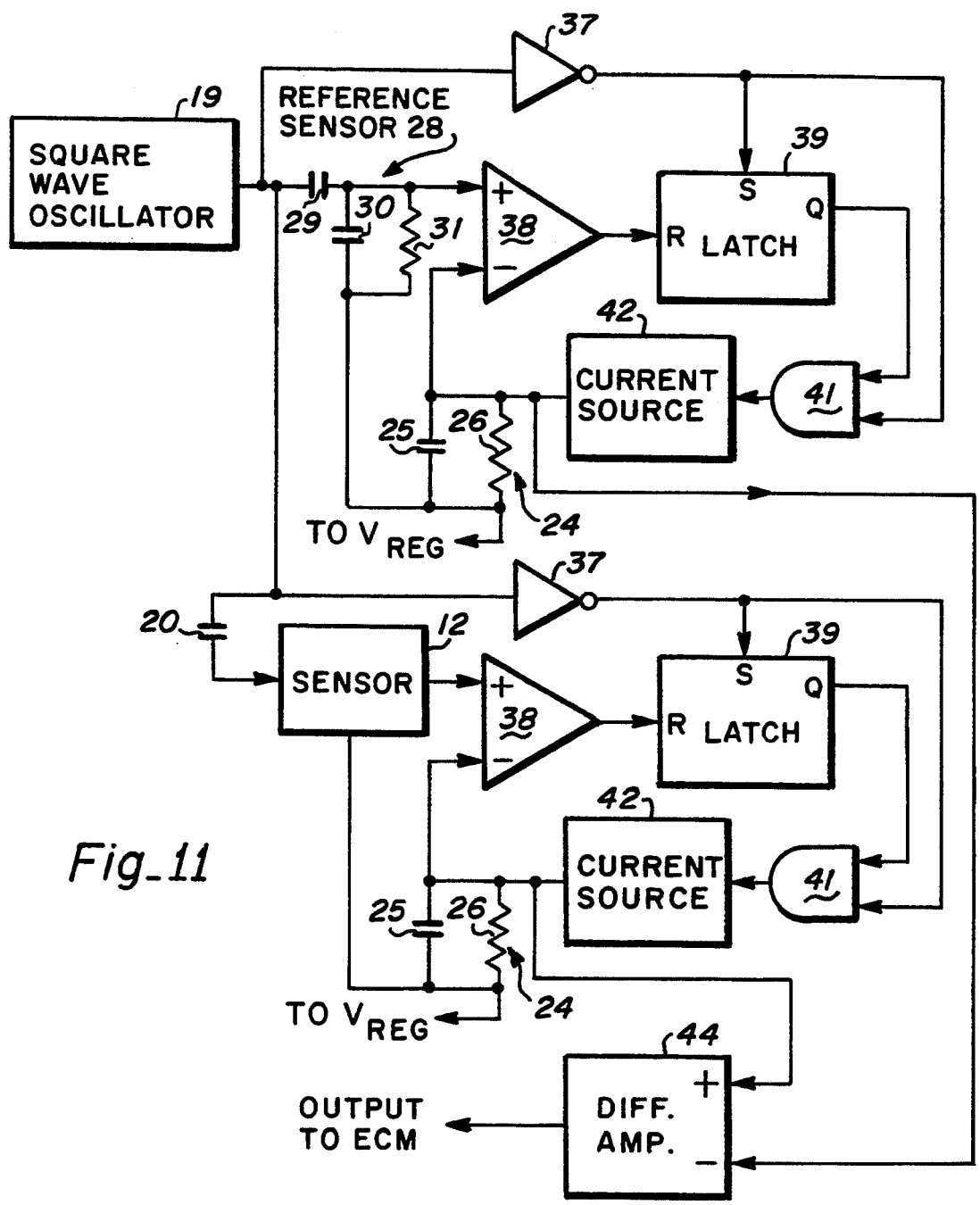
Fig_11

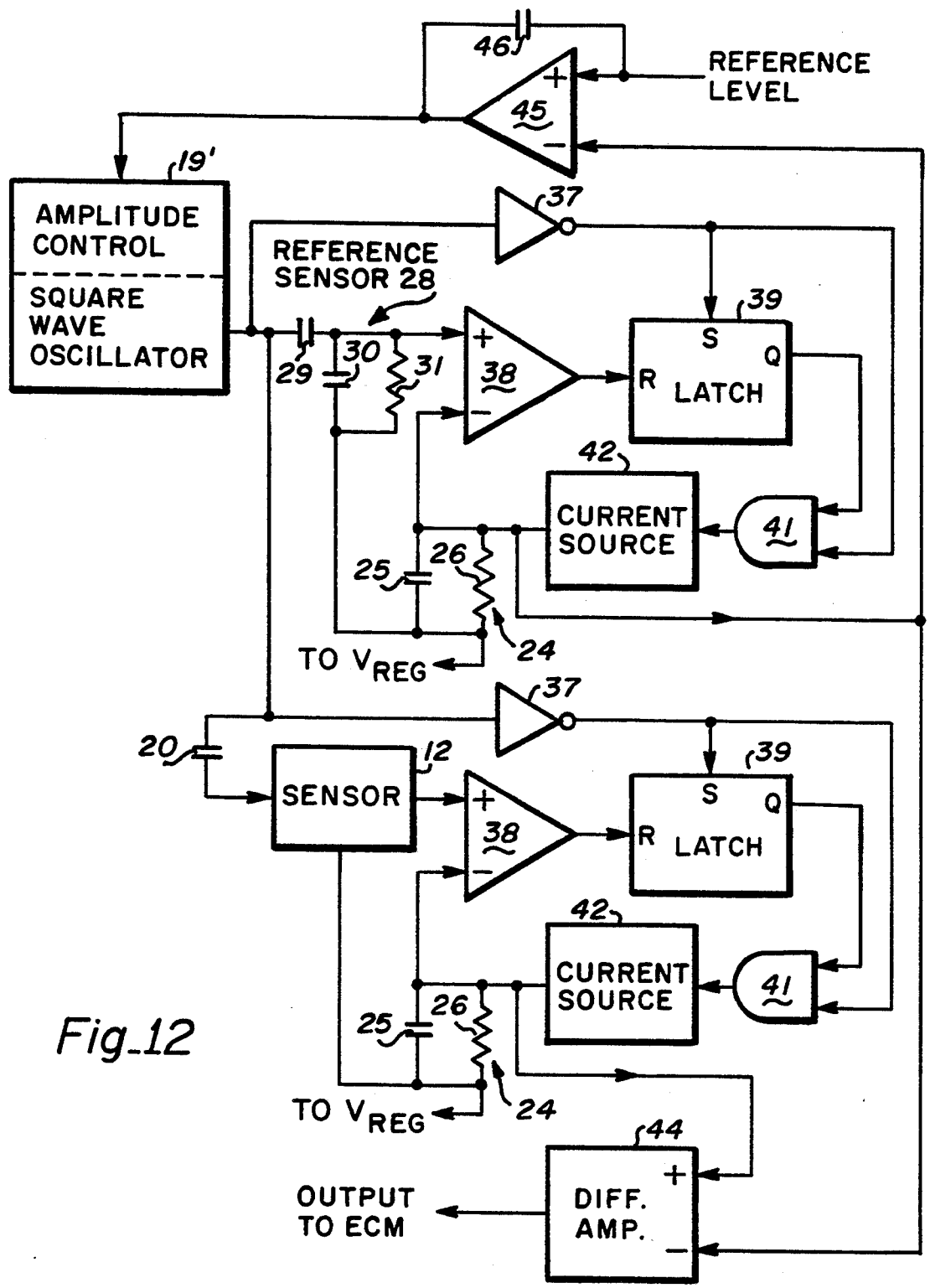
Fig_12

IC FOR PRODUCING AN OUTPUT VOLTAGE RELATED TO FUEL COMPOSITION IN A CAPACITIVE FUEL SENSOR

BACKGROUND OF THE INVENTION

The invention relates to an integrated circuit (IC) that is designed to sense the composition of a multi component automotive fuel that is used to run an engine. As the composition is sensed, the engine operation is modified for the efficient burning of the fuel. Thus, undesirable combustion products are minimized. For example, it has been found desirable to use methanol as well as gasoline to operate automotive engines. Unfortunately, the engine's fuel injection and timing must be changed when shifting from one fuel to another if efficient fuel burning is to be achieved. More desirably, the engine could be automatically adjusted to efficiently burn either gasoline, methanol or mixtures thereof. Then, it doesn't matter what fuel is present in the tank and refueling does not need to take into account what the previous refueling involved. One way to do this is to locate a fuel sensor in the engine fuel feed line and determine what fuel mixture is being sent to the engine and to use this information to program an engine control module (ECM) thereby to optimize engine performance. The sensor is located ahead of the fuel injectors at a spacing that will produce an adequate time to set engine performance as desired by the time the measured fuel reaches the engine. This delay is determined by the fuel flow rate at the optimum vehicle speed.

The fuel sensor must be capable of distinguishing between gasoline and methanol and mixtures thereof. It has been found that a capacitance measuring sensor is useful because the dielectric constants of gasoline and methanol are substantially different. As shown in FIG. 1, which displays a graph of capacitance versus percentage of methanol by volume, a substantial change in capacitance is present. Over most of the mixture range the capacitance variation is linear. For 100% gasoline the capacitance, for the test sensor, is about 28 picofarads. For 100% methanol the capacitance is about 338 pico-farads. The sensor itself consists of a fuel line section that has a small wire element located coaxially in the tubing bore. Ideally, the sensor can be located in the fuel line without measurably changing the dynamic fuel flow characteristic. If desired, a section of the fuel line is insulated from the remainder of the line and both the line and the coaxial wire are coupled to the IC. However, if uninsulated, the fuel line itself is at ground potential so the coaxial wire forms a capacitor plate that is referenced to ground.

The sensor capacitance will yield the methanol percentage whose information will be adequate to set the engine performance by way of the ECM. However, another factor must be taken into account in the form of fuel conductivity. Pure gasoline is substantially nonconductive and the introduction of a contaminant, such as water, will not significantly alter its conductivity. In the case of methanol, such water contamination will significantly alter its conductance. This change in conductance must be dealt with in the capacitance sensing system. As shown in FIG. 2, the methanol-gasoline mixture displays a strong resistance-proportion relationship. Below 30% methanol the resistance is in excess of 15 k ohms and its effect is easily avoided. However, at a 50% volume mixture the shunt resistance is about 7.5 k ohms and decreases substantially as the methanol percentage rises. More importantly as shown in curve 11, water contamination becomes significant. The water content does not significantly change engine performance and its presence does not require compensation. However, as evident in curve 11 of FIG. 2, a small amount of water will substantially increase the conductivity of the mixture. At 30% methanol the presence of water will reduce the sensor resistance from over 15 k ohms to well below 11 k ohms. At 50% methanol the shunt resistance drops from about 7.5 k ohms to about 3.5 k ohms which is about a 50% drop. Thus, it is clear that some means must be employed to avoid the shunt resistance effect if capacitive sensing is to succeed.

DESCRIPTION OF THE PRIOR ART

FIG. 3 shows the prior art approach to capacitance variation sensing that avoids the shunt resistance. Here a 10 MHz oscillator is employed to drive sensor 12. The sensor is shown composed of a shunt resistor 13 which will vary in value with the methanol percentage and the presence of fuel contamination. Capacitance 14, which varies in value in response to methanol percentage, is the component to be sensed. It has been determined that the sensor R-C time constant is typically on the order of a microsecond and varies over the range of about 2 to about 0.6 microseconds over the fuel composition range of FIG. 2. In FIG. 3, a 10 MHz oscillator 15 is coupled to sensor 12 by means of resistor 16. The resistor coupling element 16 can, in most cases, be the internal or source resistance of oscillator 15. Since a 10 MHz signal has a period of 0.1 microsecond it can be seen that virtually all of the signal current will flow in capacitor 14. This means that AM detector 17 will see a signal that is mainly determined by the value of capacitor 14. Variations in resistor 13 will have very little effect on the output of AM detector 17. Buffer 18 feeds the fuel sensor signal to the ECM and its gain can be controlled to establish the calibration of the signal to the ECM. Clearly, the 10 MHz oscillator could be operated at a higher frequency which would result in resistance 13 having even less effect. However, one of the main problems associated with the system of FIG. 3 is the radiation of the excitation signal. It is clear that any electromagnetic interference (EMI) produced will be increased as the frequency is raised. The 10 MHz frequency choice is the lowest frequency that can be employed while providing a reduced reaction by the shunt resistance of sensor 12. It is to be understood that sensor 12 is in the engine fuel line while the electronic circuitry is located elsewhere. The wire that connects the sensor to oscillator 15 will act as an antenna that will produce EMI.

Clearly, it would be desirable to operate the sensor system at a useful frequency that would reduce EMI and still avoid response to the shunt resistance of sensor 12.

An improved prior art circuit is shown in FIG. 4. It is to be understood that this figure, as well as those to follow, employ standard well-known components in the blocks. Accordingly, detailed circuits need not be discussed. A person skilled in the art will easily recognize the specific circuits that are required to perform the indicated functions.

In FIG. 4, the fuel sensor is driven from a square wave generator 19 which drives sensor 12 by way of coupling capacitor 20. Since the lower end of sensor 12 is returned to $V_{REG}$, it is grounded for signal frequencies. However, the output to AM detector 17 will include a DC component. For the sensor described in the discussion of prior art, and for which FIGS. 1 through 6 were developed, capacitor 20 can be on the order of 200 picofarads. Square wave generator 19 should produce a negative going step function having a fall time of about 50 nanoseconds. While the square wave can be symmetrical it can also be a low duty cycle pulse. Since square wave generator 19 runs continuously, after the fashion of a digital clock, it produces a square pulse having 50 nanoseconds fall at a specified 20 kHz rate. The rise time is not important and can be of the order of microseconds. The square wave fall time is short with respect to the sensor one microsecond time constant and the pulse period of 100 microseconds is long thereto. For proper voltage at the output of the AM detector output filter, the detector should only be active at the negative going edge of the square wave. Clearly, if desired, the square wave can be in the form of narrow negative going pulses which result in reduced duty cycle and lower overall current is required. Detector 17 is a simple peak detector that responds to the peak voltage across sensor 12. The magnitude of the peak voltage for a given step function will be inversely proportional to the value of capacitor 14. This relationship, while nonlinear, and can be employed to indicate the methanol-gasoline ratio in the vehicle fuel line. Buffer 18 is employed to provide a scale factor used to calibrate the output to the ECM. This is done by controlling its gain.

FIG. 5 illustrates a peak pulse detector that has been employed in the prior art FIG. 4 application. The circuit, shown in block-schematic diagram form, employs an operational amplifier (op-amp) 21 which is operated from a $V_{CC}$ power supply connected + to terminal 22 and − to ground terminal 23. The output is coupled back directly to its inverting input, and to load 24, so that 100% negative feedback is present. Thus, op-amp 21 performs as a unity gain voltage follower. Negative pulses from sensor 12 will be passed through op-amp 12 so as to charge output filter 24 to the peak value of the input pulse. Filter 24 is composed to a capacitor 25 and a resistor 26 which can respectively be 0.5 microfarads and 60 k ohms which gives an R-C time constant of 30 milliseconds. This time constant is very long compared to the period of a 20 kHz pulse rate, but is short compared to the automotive engine control period.

A voltage regulator 21 is also connected to the power supply and it provides a regulated five volt reference to detector load 24. Thus, the output will be a nominal 5 volts less the drop across load 24 which is equal to the negative peak input. FIG. 6 is a graph showing the response of FIG. 5 to the preferred sensor described above. For the minimum capacitance value, the output is slightly over a volt. For the maximum capacitance value, the output is slightly under 4 volts. The circuit of FIG. 5, while nonlinear, will produce an output that is directly proportional to the methanol fuel content.

SUMMARY OF THE INVENTION

It is an object of the invention to produce a capacitive fuel sensor having a square wave drive signal and to combine the resultant voltage with a similar voltage developed across a dummy or reference sensor so that the differential voltage is representative of the sensor response.

It is a further object of the invention to employ a square wave drive signal to energize a dummy capacitive fuel sensor and to stabilize the square wave amplitude as a function of the dummy sensor output.

It is a still further object of the invention to provide a capacitive fuel sensor with an amplitude controlled square wave drive signal that is stabilized with respect to the output of a reference sensor circuit and in which the dummy sensor output is subtracted from the fuel sensor output thereby to derive a differential output signal.

It is a still further object of the invention to provide a charge dispenser detector to develop a response to a capacitive fuel sensor driven from a square wave wherein the charge dispenser comprises a differential amplifier having one input coupled to the fuel sensor and the other input coupled to the detector output filter which is charged by the charge dispenser which is digitally operated in response to the differential amplifier output.

These and other objects are achieved in the following manner. In a basic fuel sensor, the capacitive element is driven from a square wave source having a period that is long with respect to the sensor time constant and having rise and fall times that are short with respect to the sensor time constant. The sensor is coupled to an A-M peak detector circuit which produces an output that is inversely proportional to the sensor capacitance. A reference or dummy fuel sensor is also supplied with a signal from the square wave source used to drive the fuel detector. The peak-detected output from the reference detector is used to control the amplitude of the square wave source and thereby stabilize the square wave amplitude. The outputs of the fuel and reference detectors are differentially combined to produce an output signal that is related only to the capacitance of the fuel sensor. The output signal will not be related to the sensor shunt resistance which is varied by the contamination present in the fuel being passed through the sensor. Thus, the output signal developed by combining the fuel sensor and the reference fuel sensor is inversely proportional only to the dielectric constant of the fuel.

In another embodiment, a charge dispenser peakdetector is employed. Here a square wave driven fuel sensor is coupled to one input of a differential amplifier which has an output coupled to the reset input of a latch. The set latch input is coupled to the inverted square wave drive. The latch Q output is coupled by way of a charge dispenser to an output load filter that is also coupled to the other input of the differential amplifier. In operation, the differential amplifier will control the charge on the output load to equal the charge on the fuel sensor thereby to produce an output equal to the peak level across the fuel sensor.

BRIEF DESCRIPTION OF THE DRAWING

FIG. 1 is a prior art graph showing the capacitance of a fuel sensor for various percentages of methanol mixed with gasoline.

FIG. 2 is a prior art graph showing the shunt resistance of a fuel sensor for various percentages of methanol mixed with gasoline and for a similar mixture that is contaminated with water.

FIG. 3 is a block diagram showing the elements of a prior art circuit for responding to the capacitance of a fuel sensor.

FIG. 4 is a block diagram of another basic prior art circuit.

FIG. 5 is a block diagram of an AM detector suitable for use in the FIG. 4 circuit.

FIG. 6 is a graph showing the operation of the prior art FIG. 5 circuit.

FIG. 7 is a block diagram of a dual detector circuit of the invention.

FIG. 8 is a block diagram of a dual detector version of the invention with amplitude stabilization of the square wave oscillator.

FIG. 9 is a block diagram of a circuit that employs the invention using a charge dispenser form of peak detector.

FIG. 10 is a block diagram of a circuit showing the details of the basics form of charge dispenser.

FIG. 11 is a block diagram of a circuit employing dual detection loops and means for combining the loop outputs.

FIG. 12 is a block diagram of a dual loop circuit that includes amplitude stabilization of the square wave oscillator

DESCRIPTION OF THE INVENTION

FIG. 7, which is a block diagram, shows an improved fuel sensing circuit. The upper elements are the same as the ones shown in FIG. 4. However, buffer 18' is a differential buffer which has a second input coupled to receive a reference input. In the reference channel a reference or "dummy" sensor 28 simulates a fixed element fuel sensor. This reference is composed of capacitor 30 which is selected to represent the lowest capacitance that will occur in sensor 14. With reference to the FIG. 1 conditions a capacitor value of about 25 picofarads will be used. Resistor 31 is selected to represent the lowest resistance value of resistor 13. This from FIG. 2 will typically be about 1.5 k ohms. However, resistor 31 is not critical since it is implied that the fast fall time negative transient removes most of the dependence on the resistor. Capacitor 29 and AM detector 32 will be the same respectively as capacitor 20 and AM detector 17 of FIG. 4. In this circuit differential buffer 18 will subtract the reference signal from the fuel sensor signal and its output will be linearized for use by the ECM. This provides zero-set point stability as Vout=OV when sensor capacitance equals the reference capacitance. Assuming both channels are made the same, an error cancellation effect will be provided by the reference channel. The gain of buffer 18' will determine the output scale factor as required by the ECM.

FIG. 8 shows a circuit improvement that stabilizes the operation of the fuel sensing circuit. The basic circuit is similar to that of FIG. 7. The output of AM detector 32, which comprises the reference output from reference sensor 28, is coupled to the noninverting input of op-amp 35. A capacitor 36, coupled from the inverting input of op-amp 35 to its output, converts op-amp 35 to an integrator with respect to a reference level which is a d-c potential applied to the inverting input. Thus, op-amp 35 will act as a voltage follower having high gain for d-c signals. The output of op-amp 35 is coupled to square wave oscillator 19' which includes an amplitude control function. An increase in the output of op-amp 35 will increase the amplitude of the square wave oscillator, which in turn decreases the voltage level out of the reference AM detector, so that a negative feedback loop is created to stabilize the drive to reference sensor 28. Op-amp 35 will drive the amplitude of square wave oscillator 19' until the noninverting input matches the inverting or reference input. Thus, the actual amplitude of the square wave is controlled by the d-c reference level applied to the inverting input. In this embodiment, if both channels are made similarly, device variation errors have been minimized by the use of the differential inputs of buffer 18', and square wave oscillator 19 amplitude variations have been minimized by use of the amplitude control.

FIG. 9 is a block diagram of a fuel sensor that employs an alternative peak detection circuit. Here a charge dispenser form of detector is employed. The detector load 24, which comprises capacitor 25 and resistor 26, operates as was described in connection with FIG. 5. It can be seen that both load 24 and sensor 12 are referenced to $V_{REG}$. Sensor 12 output is coupled directly to the noninverting input of comparator 38 which desirably is a high speed device. The inverting input is coupled to the detector output at filter 24. A latch 39 has its reset input coupled to the output of comparator 38 and its set input coupled by inverter 37, to the output of square wave oscillator 19. It is to be understood that latch 39 responds to the negative-going inputs and its Q output operates a charge dispenser 40 which sinks current from load 24 so to drive the potential at the inverting input of comparator 38 down. In operation, the output of comparator 38 will set the latch if the peak value of the noninverting input is less than the inverting input. The charge dispenser 40 will then be turned on for the entire low portion of the square wave oscillator 19 duty cycle thereby pulling the inverting input of comparator 38 down. The latch is set at the high portion of the square wave oscillator 19 turning off the charge dispenser 40. Thus, the voltage at the noninverting input of comparator 38 is allowed to discharge back-up towards $V_{REG}$ according to the RC time constant determined by 26 and 25. Thus, over many square wave oscillator 19 cycles, the triangle wave voltage at the inverting input of comparator 38 will peak detect the voltage at the noninverting input of comparator 38. The actual peak detection is done at the negative edge of the square wave oscillator 19. The charge dispenser 40 is allowed, during the remainder of the low portion of the square wave oscillator 19 duty cycle, to approach the peak voltage by pulling down the potential at filter 24. By allowing the peak detection function to be active for the entire low portion of the square wave, oscillator 19, instead of just the negative edge, frees the comparator 38 from having to have the high gain which is needed by the op-amp 21 in the AM detector 17 of FIG. 5. The high gain is needed since the AM detector 17 is only functional at the negative transition. The lower gain of comparator 38 will result in lower overall power consumption by the circuitry. Thus, a peak detector function is achieved in which the detection action is operative only during the negative-going portion of the sensor pulse. This substantially frees the detector of undesired responses.

FIG. 10 shows a preferred charge dispenser circuit form. The two inputs of AND gate 41 are respectively coupled to the latch Q output and the inverted square wave from oscillator 19. As was the case for FIG. 9, the circuit responds to the negative-going sensor transients and is active during the low portion of the square wave oscillator 19. The output of AND gate 41 is coupled to a constant current source 42 which pulls current out of load 24 during the set interval of latch 39. Thus, the circuit performs in a manner similar to that of FIGS. 5 and 9 and only responds to the negative portion of square wave oscillator 19.

FIG. 11 is a block diagram of a linearized fuel sensor circuit embodiment. Here square wave oscillator 19 drives fuel sensor 12 by way of capacitor 20. Sensor 12 drives the input of a charge dispenser configured as was the case for FIG. 10. The sensor output thus feeds one input of differential amplifier 44. Square wave oscillator 19 also drives reference sensor 28 by way of capacitor 29. This is the same overall configuration as presented in FIG. 7. The reference sensor 28 is coupled to a peak detector circuit having the same configuration as FIG. 10. The reference circuit output is coupled to the other input of differential amplifier 44. The reference input is subtracted from the fuel sensor input to produce an output which is employed in the ECM.

FIG. 12 is a block diagram of the preferred embodiment of the invention. The basic configuration is the same as that of FIG. 11 except that oscillator 19' includes an amplitude control function. Differential amplifier 45 has its output coupled via capacitor 46 to its inverting input to create an integrator as was described for FIG. 8. The output of the reference sensor 28 channel is coupled to the noninverting input of operational amplifier 45. The output of operational amplifier 45 is connected to the amplitude control function of square wave oscillator 19' so that the amplitude stability of the circuit created as was described for FIG. 8. This permits an externally controlled d-c level to determine the output amplitude for square wave oscillator 19'.

The invention has been described and several embodiments detailed. When a person skilled in the art reads the foregoing description, alternatives and equivalents, within the spirit and intent of the invention, will be apparent. Accordingly, it is intended that the scope of the invention be limited only by the following claims.

We claim:

1. A capacitive fuel sensor circuit for responding to the fuel sensitive capacitance developed in a fuel sensor configured to produce a fuel composition output and in which the effects of shunt resistance that results from fuel contamination are circumvented, said circuit comprising:

a square wave oscillator having its output coupled to said fuel sensor;

a first amplitude modulation detector having an input coupled to said fuel sensor and having an output related to its input;

a dummy sensor having components that simulate those of said fuel sensor;

means for coupling said output of said square wave oscillator to said dummy sensor;

a second amplitude modulation detector having an input coupled to said dummy sensor and having an output related to its input; and an output buffer having a first input coupled to said output of said first amplitude modulation detector and a second input coupled to said output of said second amplitude modulation detector whereby said fuel composition output is produced from the combined first and second amplitude modulation detector outputs.

2. The fuel sensor circuit of claim 1 wherein each of said amplitude modulation detectors is configured to respond to a negative input transient pulse and said outputs are referenced to a regulated positive voltage having a value that exceeds the maximum amplitude modulation detector output so that said circuit produces a positive output that is directly proportional to the capacitance of said fuel sensor.

3. The fuel sensor circuit of claim 1 wherein each of said first and second amplitude modulation detectors includes a low pass output filter whereby each of said outputs is a peak rectified d/c signal.

4. The fuel sensor circuit of claim 3 wherein said square wave oscillator output is controlled to have a step function fall time that is short with respect to the resistance-capacitance time constant of said fuel sensor and a pulse period that is short with respect to the low-pass filter time constant in said amplitude modulation detector.

5. The fuel sensor circuit of claim 3 wherein said first and second amplitude modulation detector outputs are subtractively combined in said output buffer.

6. The fuel sensor circuit of claim 3 wherein said square wave oscillator includes an amplitude control function having a control input coupled to respond to the output of said second amplitude modulation detector whereby said square wave amplitude is stabilized.

7. The fuel sensor circuit of claim 3 wherein said first and second amplitude modulation detectors each comprise:

a comparator having inverting and noninverting inputs and an output;

means for coupling the signal to be detected to said noninverting comparator input;

a latch having its reset input coupled to said comparator output, its set input coupled to an inverted version of said square wave oscillator output, and having an output related to its reset input; and a charge dispenser having its input coupled to said output of said latch and an output coupled to said inverting input of said comparator and to said low pass filter whereby the signals coupled to said comparator noninverting input are peak detected at said charge dispenser output.

8. The fuel sensor circuit of claim 7 wherein said comparator noninverting input is responsive to negative-going transients from said square wave oscillator, said charge dispenser is configured to sink current, and said low pass filter along with said sensor is referenced to a regulated positive supply voltage whereby said charge dispenser output is a voltage that is directly proportional to said sensor capacitance.

* * * * *

UNITED STATES PATENT AND TRADEMARK OFFICE
CERTIFICATE OF CORRECTION

PATENT NO. : 5,343,156
DATED : August 30, 1994
INVENTOR(S) : Nick M. Johnson and Chun-Foong Cheah It is certified that error appears in the above-identified patent and that said Letters Patent is hereby corrected as shown below:

Cover Page, Column 1, add:

Assignee: National Semiconductor Corporation
Santa Clara, California

Signed and Sealed this

Seventh Day of February, 1995

Attest:

BRUCE LEHMAN

*Attesting Officer*     *Commissioner of Patents and Trademarks*